United States Patent [19]

Wang

[11] 4,436,826

[45] Mar. 13, 1984

[54] TAGGED IMMUNOASSAY

[75] Inventor: Chia-Gee Wang, Millwood, N.Y.

[73] Assignee: Wang Associates, Millwood, N.Y.

[21] Appl. No.: 313,711

[22] Filed: Oct. 21, 1981

[51] Int. Cl.³ .................... G01N 33/54; G01N 33/56
[52] U.S. Cl. ...................... 436/525; 422/68;
436/533; 436/534; 436/829
[58] Field of Search ............... 23/230 B, 915, 920;
424/12; 422/68, 73; 250/461 B; 436/533, 534,
525, 526, 829

[56] References Cited

U.S. PATENT DOCUMENTS

| | | | |
|---|---|---|---|
| 3,853,987 | 12/1974 | Dreyer | 23/230 B X |
| 4,022,577 | 5/1977 | Brooker et al. | 23/230 B |
| 4,108,972 | 8/1978 | Dreyer | 23/230 B X |
| 4,108,976 | 8/1978 | Reese | 23/230 B X |
| 4,177,253 | 12/1979 | Davies et al. | 23/230 B X |
| 4,205,952 | 6/1980 | Cais | 23/230 B |
| 4,219,335 | 8/1980 | Ebersole | 23/230 B |
| 4,283,382 | 8/1981 | Frank et al. | 23/230 B X |
| 4,297,337 | 10/1981 | Mansfield et al. | 424/12 X |
| 4,313,734 | 2/1982 | Leuvering | 23/230 B |

OTHER PUBLICATIONS

Voller et al., "Immunoassays for the 80's", University Park Press, Baltimore, Md., 1981, pp. 35–41.
Ron Jenkins et al., "Quantitative X-ray Spectrometry", Marcel Dekker, Inc., New York, and Basel, 1981, pp. 101–107.
"Practical Radioimmunoassay", A. J. Moss, Jr., 1976, the C. V. Mosby Co., St. Louis, Mo., p. 139.

*Primary Examiner*—Arnold Turk
*Attorney, Agent, or Firm*—Ladas & Parry

[57] ABSTRACT

An immunoassay method for measurement of the content of a target antigen or antibody in a fluid or tissue specimen comprises reacting the target with reagent antibody or antigen which forms a complex with the target and is tagged with tagging elements which are unassociated chemically with said reagent and are protected against reaction with the target and the biological and chemical environment of the assay. Preferably the reagent antibody or antigen is carried by small, tagged mobile units, such as latex particles of a size smaller than 0.8 μm, having tagging elements embedded therein. The tagged complexes which are formed may be measured by X-ray fluorescence or by detection of radioactive decay. Different target antigens or antibodies can be assayed simultaneously by employing different tagged mobile units, and the mobile units with the tagging elements can be recovered for disposal or for reuse.

46 Claims, 3 Drawing Figures

FIVE STEPS OF TIA

TAGGED IMMUNOASSAY

BACKGROUND OF THE INVENTION

1. Field of the Invention

This invention relates to an immunoassay method, and to apparatus for carrying out the method. More specifically, the invention relates to an immunoassay method for measurement of the quantity of one or more antigens or antibodies, hereinafter called target antigens or antibodies, in a fluid or tissue specimen. The target antigens or antibodies to be quantitatively determined are reacted with tagged antibodies or antigens which form a complex with the target, and the formed complexes are counted by detection of the tagging elements.

2. Description of the Prior Art

Radioimmunoassay (RIA) is currently the best developed method of immunoassays. A radioactive isotope, usually I-125, is used to label a known antigen (hereinafter called Ag), and the labeled Ag (Ag*) competes with the target Ag of a specimen for the binding site of a given amount of "monomeric" antibody (hereinafter called Ab). The radioactivity of the Ag*-Ab precipitants, often with a second species specific Ab for precipitation, inversely indicates the amount of non-radioactive Ag-Ab complexes in the system, and therefore the amount of the target Ag of the specimen. When instead the antibodies are labeled (Ab*) to directly measure the Ag or ligand, rather than use of Ag* and a limited amount of Ab, the technique is called immunoradiometricassay (IRA). There are about $5 \times 10^{16}$ Ab per ml in a typical animal serum, with each Ab typically having about 20,000 atoms and a molecular weight of about 150,000. If there are 5 million kinds of Ab, each kind would on the average have $10^{10}$ copies per ml. This abundance in copies and richness in variety are what make the immunoassays so easy to prepare and so powerful a tool for measurement.

There are, however, several drawbacks in a method as powerful as RIA. If labeled iodine appears at the sensitive position of the Ag, i.e., the epitope, it would alter the immune affinity. Incubation time for RIA, especially when a second antispecies globulin is used for precipitation, is too long. The presence of agglutinating elements in a specimen such as the serum rheumatoid factor (RF) and the Clq unit of the complement can often give rise to unintended agglutinations. But by far, the most serious problem of the method has been the disposal of voluminous radioactive waste.

Since the discoveries of RIA and IRA, a major improvement has been the introduction of solid phase systems. With a solid phase, Ab or Ag are absorbed or covalently conjugated onto a matrix such as cellulose, polystyrene (latex) or polyacrylamide to form an "immobilized system". The solid phase system can be in the form of a wall or beads, can give easy and precise separation of bound from free, requires fewer manipulations, and provides lower non-specific bindings. Other immune assays such as fluoroimmunoassay, enzymoimmunoelectrophoresis, etc., can also use the solid phase systems to take advantage of their inherent ease of bringing reagents into the assay and of separating bound from free.

With a sufficiently small solid phase system, the mobility of the solid phase units can also be exploited. In particle immunoassay (PIA), for example, 0.8 $\mu$m latex beads are each coated by $10^5$ Ab. The coated beads can react like the Ag-Ab complexes with respect to the agglutinating agents such as RF, Clq, or the murine agglutinators. In a PIA, Ag-Ab complexes compete for the agglutinators with a given amount of the coated beads, while the residual, non-agglutinated beads become proportional to the amount of Ag of the specimen. The beads are counted by their scattering of light. A review of various immune methods can be seen from "Immunoassays for the 80s," edited by Voller et al., University Park Press, Baltimore, Md., 1981. In this publication, PIA is described in an article by P. L. Masson et al. on pages 35–41.

In such known labeled immunoassays, the labeling elements, which can be radioactive or fluorescent, are conjugated to the Ag or Ab and exposed to the assaying chemistry. They cannot easily be separated from the system even with the aid of solid phase units. For PIA, light photons are used to count the single beads discriminately, so that the beads must have a dimension of greater than 0.8 $\mu$m, about twice the photon wavelength, in order to be observable. Compared to the size of an Ab, the bead is two to three orders of magnitude larger in its longest linear dimension, so that the thermodynamic and chemical characteristics of the bead are very different from those of the Ab. As a result, agglutinating agents must be used in PIA.

SUMMARY OF THE INVENTION

According to the present invention, there is provided an immunoassay method for measurement of the content of a target antigen or antibody in a fluid or tissue specimen, which comprises reacting the target with reagent antibody or antigen which forms a complex with the target and is tagged with tagging elements or compounds which are unassociated chemically with said reagent and are protected against reaction with the target and the biological and chemical environment of the assay, and detecting the formed, tagged complexes.

Preferably, the reagent Ab or Ag is carried by small tagged mobile units such as latex particles. The tagged mobile units coupled with Ab or Ag are reacted with the target Ag or Ab, the unreacted mobile units are separated and the number of reacted mobile units is measured by measurement of the tagging elements, for example by X-ray fluorescence or by detection of radiation.

Also provided in accordance with the present invention is an immunoassay apparatus for measuring the content of a target antigen or antibody in a fluid or tissue specimen, which comprises a container for said fluid or tissue specimen, means for introducing the specimen to the container, means for sequentially introducing to the specimen small tagged mobile units carrying reagent antibody or antigen, and a detector for measuring tagging elements of said tagged mobile units.

DESCRIPTION OF THE PREFERRED EMBODIMENTS

The present invention provides a new method of tagged immunoassay, hereinafter referred to as TIA.

This new method is particularly adapted to measure Ag or Ab in fluids such as serum and tissues such as nerve tissue.

Small, tagged latex particles are preferably used in the present method. Such small latex particles conjugated by Ab or Ag can participate in an immunoassay as if they are mobile units of Ab or Ag, and thus are referred to herein as small, tagged mobile units. According to the present invention, it is preferred that the size (longest linear dimension) of said mobile units is smaller than 0.8 $\mu$m. More preferably the tagged mobile units are smaller than 0.34 $\mu$m, and still more preferably, they are smaller than 0.1 $\mu$m. In a particularly preferred embodiment, the tagged mobile units have a size in the range from 0.1 $\mu$m to 0.008 $\mu$m.

The mobile units are tagged with tagging elements or compounds which may comprise any elements that can be detected, such as by X-ray fluorescence or by measurement of radioactive decay. Preferably the tagging elements are heavy tagging elements which have an atomic weight in excess of 50. Examples of these are Fe, Ni, Cu, Co, and the like.

Thus, the method of the present invention preferably employs small mobile units, particularly latex particles, which are one to two orders of magnitude smaller than the 0.8 $\mu$m particles used in the above-mentioned PIA method. With such smaller particles, the avidity of the Ag-Ab bonds makes it possible to separate bound particles from free particles. This makes the affinity relationship of the Ag-Ab complexes inherently Ag specific, giving rise to the possibility of assaying many Ag-Ab complexes from the same specimen. Also the tagged elements can be embedded into the mobile units unexposed to the chemical reactions of the assay, providing the possibility that a variety of "unstable" or reactive tags can be used and be recovered from the assay. The measuring device to detect the tags can be very simple, yet the method provides high sensitivity, specificity, accuracy, and precision.

Figure 1:
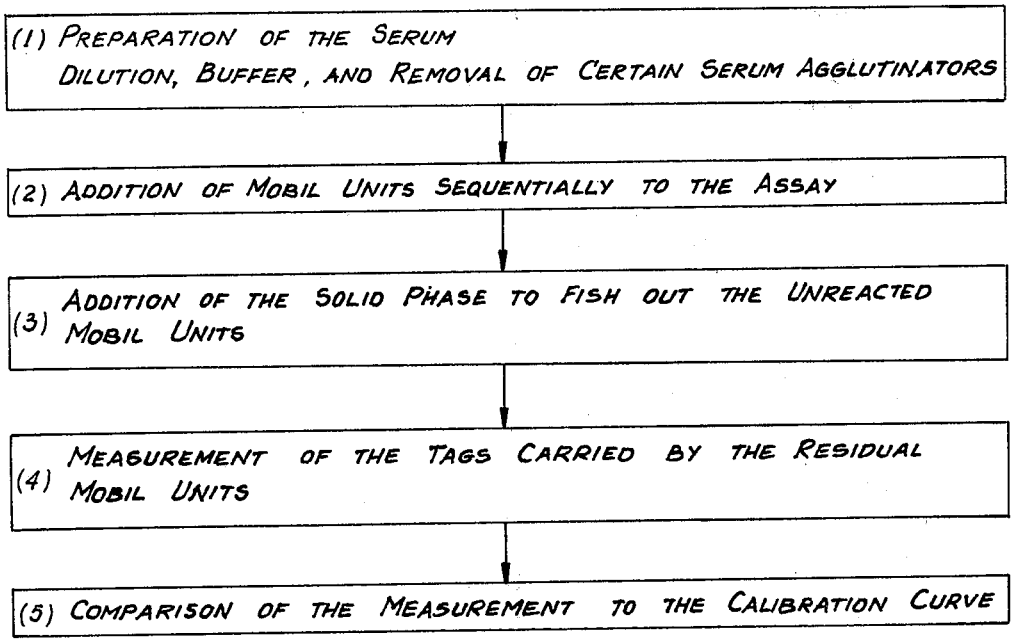
FIG. 1 is a diagrammatic representation of the preferred steps of the present method.

The TIA method of the present invention has the advantage of being extremely simple and convenient. It will now be described with reference to the drawing. Preferred steps of the method of the present invention are shown in FIG. 1 which illustrates the assay of the target Ag (or Ab) of a serum specimen. First, serum is diluted, buffered, and passed through a solid phase where necessary to remove certain agglutinators and to avoid unintended agglutinations of the mobile units. The reagent of the initial removal solid phase can be a certain "activated Ab" conjugated on a large latex matrix. Second, a chosen amount of the mobile units coupled with the specific Ab(or Ag) is added to the system to react with the target Ag(or Ab) in an incubation. Third, the same kind of the target Ag(or Ab) in a solid phase is added to "fish out" or remove the unreacted mobile units in a short incubation without allowing the complexes of the mobile Ag-Ab units and the solid phase Ag-Ab to reach concentration equilibrium. Fourth, the residual mobile units not deleted by the solid phase are concentrated and counted by the presence of their tags. Finally, the measurement is compared with a calibration curve of the Ag(or Ab) concentrations measured by the same amount of the mobile units and the solid phase systems prepared from the same batch. That is, the measurement is compared with a calibration curve of known target antigen or antibody concentration plotted against X-ray fluorescence measurement. The last step is to remove the systematic errors, as Ab, even from the same animal, can vary from batch to batch, and this practice has been common in a variety of immunoassays. The five steps listed above can be combined in an automated measuring apparatus.

Figure 2:
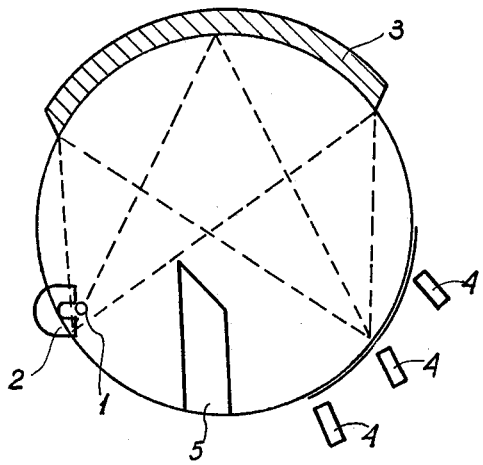
FIG. 2 is a plan view of the present apparatus including X-ray fluorescent detector as the preferred detector.

FIG. 2 depicts an embodiment of the apparatus of the present invention based on measurement of X-ray fluorescence, in which a container 1 for a fluid or tissue specimen is positioned near an X-ray tube or radioactive source 2, which excites the specimen. The resulting beam of radiation impinges on a Johansson bent crystal 3 which disperses the different wavelengths of X-ray photons emitted by the specimen, the dispersed radiation being directed to the region of X-ray detectors 4 where different detector positions correspond to different tagging elements. X-ray detectors 4 can be replaced by X-ray film. A shield 5 is typically included. The technique and apparatus of X-ray fluorescence spectrometers is now fully described in "Quantitative X-ray Spectrometry", by Ron Jenkins et al., 1981, Marcel Dekker, Inc., New York and Basel, the disclosure of which is incorporated herein by reference. A general discussion of instrumentation may be found in said publication on pages 101–107.

Figure 3:
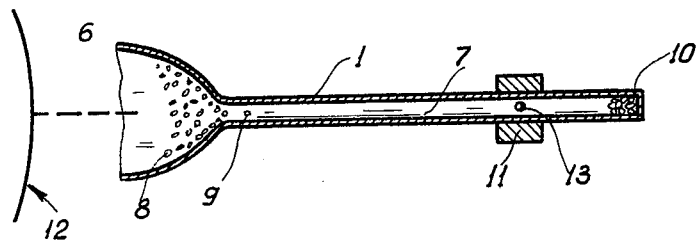
FIG. 3 is a sectional side view of the specimen container of the present apparatus.

The container for the specimen is shown more fully in FIG. 3 in which the specimen container 1 is shown to have an inlet 6 for admitting fluid or tissue, and an elongated section 7. By means of a centrifuge, a part 12 of which is shown generally, and to which container 1 is attached, mobile units 8 are directed into elongated section 7, and move through the elongated section 7 towards the end 10 sequentially, as shown at 9, under the centrifugal field, for reaction with the specimen Ag or Ab.

A solid phase latex 11 has Ag or Ab thereon which forms a complex with unreacted reagent Ab or Ag and removes free mobile units. Latex 11 is in contact with the specimen through an opening 13 in elongated section 7, or may be located within section 7.

The bound mobile units not removed on latex 11 move to end 10 of elongated section 7 where they are concentrated. End 10 of specimen container 1 can be positioned adjacent to the X-ray tube or radioactive source 2 shown in FIG. 2.

In a competitive binding assay such as RIA, reagents compete for the same binding sites and their order of joining the assay is not important as long as the reagents can reach certain equilibrium. In a direct binding assay such as IRA or TIA, the binding site once occupied with sufficient avidity, can become "inseparable". If each mobile unit carries only one Ab or Ag, again the order of joining the assay is unimportant. But with each mobile unit carrying on the average 10 or 100 Ab or Ag, it becomes essential to have some of them completely neutralized in the formation of the immune complexes, while the other remain relatively free of the complex. A means of accomplishing this is for the mobile units to be introduced sequentially, as shown in FIG. 3. The arrangement of a relative crosscurrent would not only assure the sequential occupation of the binding sites, but also aid to the automated designs. A spin down of the mobile units in a centrifugal field would provide sufficient movements relative to the specimen liquid. The mobile units can also be magnetically controlled if the tags are made of magnetic material, although great care must be taken concerning demagnetization of the tags. Another way of accomplishing the reaction so that some mobile units are completely bound and others are relatively free of the complex is to introduce the mobile units to the specimen in small increments for stepwise reaction with the target Ag or Ab.

In RIA, the radioactivity of Ag*-Ab is inversely proportional to the amount of Ag. In IRA or TIA, the direct binding gives a linear relationship between the tags measured and the amount of the target Ag or Ab. An error analysis can show that the linear relationship gives a larger range of accurate calibration while the inverse relationship must limit the most accurate range at the place where the amount of complexes between Ag*-Ab and Ag-Ab are about the same.

About 10 amino acids are required to form an epitope; the sensitive portion of an Ag. Haptens are generally too small a molecule to be recognized as an Ag, and often must be combined with a substrate protein in order to participate in an immunoassay. Using the substrate protein as an Ag, Hapten can then become an inhibitive agent when it forms a ligand with the Ag as it changes the immune affinity. This change of the immune affinity can become a means for measuring hapten by the present TIA method. There are many compounds which can participate with the commonly used substrate protein to alter their specificity, so that this inhibitive means of measuring hapten may or may not be accurate by choice.

Thus, the present TIA method can provide higher sensitivity than RIA or IRA in general, and can in fact provide the highest sensitivity amongst all the known immunoassays for most Ag and Ab. The immune affinity is fully explored for the agglutination in TIA, so that multiple kinds of Ag or Ab can be measured in the same specimen with very high specificity. Direct binding gives a linear relationship on the calibration and provides a high accuracy for a large range of the target concentrations. Tags can be made of elements independent of the biological and chemical environment of the assay, and thereby the assay can be reproduced for high precision.

For use in the present invention, small tagged mobile units can be formed in a number of ways. Latex beads, such as those supplied by Polyscience, Inc. (Paul Valley Industrial Park, Warrington, Pa. 18976), or E. F. Fullam Inc. (900 Albany-Shaker Road, Lathan, N.Y. 12110) can be ordered for dimensions much less than 0.1 $\mu$m. The lyophilized beads can be spread out on the surface of a low vapor pressure liquid to avoid the beads stacking upon each other. Metals, serving as the tagging elements, can be ion implanted into the beads in a system which includes the supporting liquid. The depth of penetration of the ion beam is easily adjusted by settings of the accelerating voltage, and a penetration of about 5 nm would serve nicely. A variety of metals can be selected as the source of the embedded elements, and their chemical stability as shielded by the latex matrix is not important. For the determination of multiple kinds of Ag or Ab, each embedded element as tag must correspond to a particular reagent Ab or Ag for its target Ag or Ab.

The tagged mobile units may also be formed by mixing tagging elements with the latex and forming precursor beads, or coating precursor beads with the tagging elements. A further coating of latex may then be applied, thereby forming the small mobile units.

An alternative to ion implantation is simply a vapor coating of a layer of metal, perhaps 20 nm thick, on one side of the beads, followed on the same side by a second coating with a stable element or compound to isolate the metal if necessary. Reagent Ab or Ag are to be conjugated on the bare side of the latex matrix. If a more exact configuration of the mobile units is desired, such as in the form of a cylinder or a cube where a relatively flat surface can be used to conjugate the reagent Ab or Ag, the vapor coating can be performed on large thin latex sheet, and by pressing the coated faces together, the tagging element becomes sandwiched in the middle. An electron or ion beam focused on the sheet can cut it into little circles or squares. The cut edges can be sealed, e.g. by formation of an oxide of the exposed tagging elements, when necessary. The focusing dimension of the beam can be much smaller than that of the mobile units, and with the beam-scan electronically controlled, the cutting patterns can be generated very quickly.

The coupling of protein onto latex matrix is known for a long time, and is routinely used by various designs of solid phase systems. Bio-Rad Labs (2200 Wright Ave., Richmond, Ca. 94804), for example, provides a reagent coupling kit EDAC which couples the latex matrix and the reagent by carbodiimide. The matrix can be conjugated directly by Ab or Ag, or by a species specific anti-Fc globulin first and then the specific Ab in order to assure that the (Fab')$_2$ portion of the specific Ab retains its full immune affinity, or that only the (Fab')$_2$ portion is conjugated with the Fc section cleaved off by the enzyme pepsin in order to avoid Fc related agglutinations. The coupling of the reagent onto the latex matrix can be followed by the tagging process if necessary.

In RIA, each Ag* can be labeled with an I-125 and it competes with the cold, target Ag. About $10^7$ labeled Ag* or the Ag*-Ab complexes are required to provide a meaningful signal of 100 counts per minute. Assume that the mobile units of TIA are also tagged with $10^7$ atoms each, and if they are also radioactive isotopes such as I-125, and with each mobile unit conjugated on the average by 10 Ag, then the present TIA method becomes more sensitive than RIA by a factor of $10^6$, provided of course that the radiation exposure is short enough such that the affinity and the avidity are not seriously altered. Furthermore, the mobile units can be recovered for easy disposal in a concentrated volume, or even for reprocessing.

In a X-ray fluorescent analysis of trace metals, the relative sensitivity is about $10^{-6}$ g per ml, with the metal's molecular weight at about 60. This value implies a sensitivity of the tags at $10^9$ per ml. With a sampling volume for the X-ray analysis at $10^{-2}$ ml, the sensitivity becomes $10^7$ tags per sampling. The mobile units can be highly concentrated by centrifugation, or they can be agglutinated by another stage of solid phase separation in order to lump them together for measurement. With agglutinated mobile units for measurement, the TIA method of the present invention with X-ray fluorescence can be more sensitive than RIA by a couple of orders of magnitude. In order to perform the final stage of solid phase agglutination, certain design considerations must be incorporated into the mobile units. When using the PIA method of agglutination, for example, the mobile unit must be coated with whole Ab in order to have the Fc section to react with the agglutinator. If higher sensitivity is desired, the X-ray fluorescent analysis can be pushed by six or more orders of magnitude by incorporating a focused electron beam to excite the tagging elements.

In RIA and IRA, radioactive isotopes such as CO-57, H-3, C-14, and I-125 can replace their non-radioactive counterparts as labels. In addition, with catalysts such as Chloramine-T, oxidizing enzymes, or with electrolysis etc., I-125 can react with various reagent proteins and serve as the most commonly used label. Using different isotopes in these methods, several kinds of Ag-Ab complexes can in principle be assayed in the same batch. But in practice, with limits of detector resolution, and with I-125 as the common label for proteins, usually only one kind of Ag-Ab complex is measured in an assay. In the TIA method of the present invention, the tagged elements can be incorporated into the system regardless of the biochemical environment, and various elements can therefore be designed simply for the convenience of the detector sensitivities. A X-ray film in place of the photo-detectors in FIG. 2, for example, can simultaneously record and distinguish many elements, say ten or more, according to their characteristic fluorescent X-ray lines. The specificity of the agglutinations and the freedom of assigning the tagged elements are what enable the present TIA method to assay multiple Ag-Ab complexes simultaneously and with ease.

Currently used and available RIA kits can also be used in the present TIA method, as the specific Ab to bind the Ag such as:
  adrenocorticotropin
  aldosterone
  angiotensin
  barbiturates
  carcinoembryonic antigen
  cortisol
  digitoxin estrogen
  folic acid
  follicle-stimulating hormone
  gastrin
  gentamicin
  hapatitis associated antigen
  human chorionic gonadotropin
  human growth hormone
  human placental lactogen-human chorionic somatotropin
  immunoglobulin E
  Insulin
  morphine
  testosterone
  thyroid stimulating hormone
  thyroxine and triiodothyroxine
  Vasopressin
  Vitamin $B_{12}$.

Such Kits are further described in "Practical radioimmunoassay" A. J. Moss, Jr., 1976, the C. V. Mosby Company, Saint Louis, Mo., the disclosure of which is incorporated herein by reference, especially starting on page 139.

I claim:

1. An immunoassay method for measurement of the content of a target antigen or antibody in a fluid or tissue specimen, which comprises reacting the target with reagent antibody or antigen which forms a complex with the target and is tagged with tagging elements or compounds which are unassociated chemically with said reagent and are protected against reaction with the target and the biological and chemical environment of the assay, and detecting the formed, tagged complexes.

2. A method according to claim 1, wherein the tagging elements or compounds are protected by being embedded within small latex particles.

3. A method according to claim 2, wherein the tagging elements or compounds were embedded by ion implantation into said latex particles.

4. A method according to claim 2, wherein the tagging elements or compounds were embedded by vapor coating onto a portion of the surface of a latex particle, followed by further coating the vapor coated portion of the latex particle with an element or a compound which is non-reactive with the target and the biological and chemical environment of the assay.

5. A method according to claim 2, wherein the tagging elements or compounds were embedded by coating thin latex sheets with the tagging elements or compounds, pressing the coated surfaces of two sheets together to form a composite sheet and cutting the composite sheet with an electron or ion beam into particles.

6. A method according to claim 2, wherein the small latex particles carry a plurality of reagent antibody or antigen molecules and said particles are sequentially introduced to the specimen for reaction with the target antigen or antibody.

7. A method according to claim 2, wherein the small latex particles carry a plurality of reagent antibody or antigen molecules and said particles are introduced to the specimen in small increments for reaction with the target antigen or antibody.

8. A method according to claim 1, wherein the reagent antibody or antigen is tagged with heavy tagging elements which have an atomic weight in excess of 50.

9. A method according to claim 1, wherein the tagged complexes are detected by X-ray fluorescence.

10. An immunoassay method for measurement of the content of a target antigen or antibody in a fluid or tissue specimen, which comprises reacting the target with reagent antibody or antigen which forms a complex with the target and is carried by small tagged mobile units having tagging elements or compounds which are unassociated chemically with said reagent and are protected against reaction with the target and the biological and chemical environment of the assay, and detecting the tagged mobile units bearing formed complexes.

11. A method according to claim 10, wherein the tagged mobile units are smaller than 0.8 μm.

12. A method according to claim 10, wherein the tagged mobile units are smaller than 0.35 μm.

13. A method according to claim 10, wherein the tagged mobile units are smaller than 0.1 μm.

14. A method according to claim 10, wherein the mobile units have a size in the range from 0.1 μm to 0.008 μm.

15. A method according to claim 10, 12 or 13, wherein said mobile units are latex particles.

16. A method according to claim 15, wherein the tagging elements or compounds are protected by being embedded within said latex particles.

17. A method according to claim 16, wherein the tagging elements or compounds were embedded by ion implantation into said latex particles.

18. A method according to claim 16, wherein the tagging elements or compounds were embedded by vapor coating onto a portion of the surface of a latex particle, followed by further coating the vapor coated portion of the latex particle, with an element or a compound which is non-reactive with the target and the biological and chemical environment of the assay.

19. A method according to claim 16, wherein the tagging elements or compounds were embedded by coating thin latex sheets with the tagging elements or compounds, pressing the coated surfaces of two sheets together to form a composite sheet, and cutting the composite sheet with an electron or ion beam into particles.

20. A method according to claim 10, wherein the reagent antibody or antigen is tagged with heavy tagging elements which have an atomic weight in excess of 50.

21. A method according to claim 10, wherein the tagged mobile units carrying reagent antibody or antigen are sequentially introduced to the specimen for reaction with the target antigen or antibody.

22. A method according to claim 10, wherein the tagged mobile units carrying reagent antibody or antigen are introduced to the specimen in small increments for reaction with the target antigen or antibody.

23. A method according to claim 10, wherein the tagged complexes are detected by X-ray fluorescence.

24. An immunoassay method for measurement of the content of a target antigen or antibody in a fluid or tissue specimen, which comprises coupling reagent antibody or antigen, which forms a complex with the target, with small tagged mobile units having tagging elements or compounds which are unassociated chemically with said reagent and are protected against reaction with the target and the biological and chemical environment of the assay, reacting the tagged mobile units coupled with antibody or antigen with the target antigen or antibody, separating the unreacted mobile units and measuring the number of reacted mobile units by detection of the tagging elements or compounds.

25. A method according to claim 24, wherein the tagged mobile units are smaller than 0.8 $\mu$m.

26. A method according to claim 24, wherein the tagged mobile units are smaller than 0.35 $\mu$m.

27. A method according to claim 24, wherein the tagged mobile units are smaller than 0.1 $\mu$m.

28. A method according to claim 24, wherein the mobile units have a size in the range from 0.1 $\mu$m to 0.008 $\mu$m.

29. A method according to claim 24, 26 or 27, wherein said mobile units are latex particles.

30. A method according to claim 24, wherein the tagging elements or compounds are protected by being embedded within said latex particles.

31. A method according to claim 30, wherein the latex is polystyrene.

32. A method according to claim 30, wherein the tagging elements or compounds were embedded by ion implantation into said latex particles.

33. A method according to claim 30, wherein the tagging elements of compounds were embedded by vapor coating onto a portion of the surface of a latex particle, followed by further coating the vapor coated portion of the latex particle with an element or a compound which is non-reactive with the target and the biological and chemical environment of the assay.

34. A method according to claim 30, wherein the tagging elements or compounds were embedded by coating thin latex sheets with the tagging elements or compounds, pressing the coated surfaces of two sheets together to form a composite sheet and cutting the composite sheet with an electron or ion beam into particles.

35. A method according to claim 24, wherein the reagent antibody or antigen is tagged with heavy tagging elements which have an atomic weight in excess of 50.

36. A method according to claim 24, wherein the tagged mobile units carrying reagent antibody or antigen are sequentially introduced to the specimen for reaction with the target antigen or antibody.

37. A method according to claim 24, wherein the tagged mobile units carrying reagent antibody or antigen are introduced to the specimen in small increments for reaction with the target antigen or antibody.

38. A method according to claim 24, wherein undesired agglutinator compounds are removed from the fluid or tissue containing target antigen or antibody before the reaction with tagged mobile units coupled with antibody or antigen.

39. A method according to claim 38, wherein said agglutinator compounds are removed by contacting them with activated antibody conjugated to a latex matrix.

40. A method according to claim 24, wherein said unreacted mobile units are separated by contacting the fluid or tissue with added antigen or antibody which is the same as the target antigen or antibody and is conjugated to a solid phase matrix, incubating for a short time, and separating said fluid or tissue from said solid phase matrix.

41. A method according to claim 24, wherein after said separation of unreacted mobile units the remaining reacted mobile units are concentrated or agglutinated prior to detection of the tagging elements or compounds.

42. A method according to claim 24, wherein the tagging elements of the reacted mobile units are measured by X-ray fluorescence.

43. A method according to claim 24, wherein the tagging elements are radioactive and the number of reacted mobile units it measured by detection of radioactivity.

44. A method according to claim 42, wherein the measurement is compared with a calibration curve of known target antigen or antibody concentration plotted against X-ray fluorescence measurement.

45. A method according to claim 42 of 43, wherein after the measurement the reacted mobile units are recovered for disposal or reprocessing for reuse.

46. A method according to claim 24, wherein the contents of different target antigens or antibodies in said fluid or tissue are simultaneously measured by reacting with each different target tagged mobile units which have tagging elements or compounds specific to each target and which are coupled with antibody or antigen specific to each target, and measuring the number of reacted mobile units of each different complex in the same fluid or tissue specimen by detection of the different X-ray fluorescence of each different tagging element.

* * * * *